(12) United States Patent
Butani et al.

(10) Patent No.: US 11,207,036 B2
(45) Date of Patent: Dec. 28, 2021

(54) SYSTEM AND METHOD FOR CABINET X-RAY SYSTEMS WITH AUTOMATIC SPECIMEN/SAMPLE ALERT

(71) Applicant: KUB Technologies, Inc., Stratford, CT (US)

(72) Inventors: Vikram Butani, Stratford, CT (US); Yan Chen, Stratford, CT (US); Chester Lowe, Stratford, CT (US); Vignesh Mandalapa-Bhoopathy, Stratford, CT (US); Edwin Maria-Selvaraj, Stratford, CT (US); Roberto Velasco, Stratford, CT (US)

(73) Assignee: KUB Technologies, Inc., Stratford, CT (US)

( * ) Notice: Subject to any disclaimer, the term of this patent is extended or adjusted under 35 U.S.C. 154(b) by 525 days.

(21) Appl. No.: 15/999,113

(22) Filed: Aug. 16, 2018

(65) Prior Publication Data

US 2019/0053771 A1   Feb. 21, 2019

Related U.S. Application Data

(60) Provisional application No. 62/546,338, filed on Aug. 16, 2017.

(51) Int. Cl.
*A61B 6/00* (2006.01)
*A61B 6/02* (2006.01)
(Continued)

(52) U.S. Cl.
CPC ............. *A61B 6/025* (2013.01); *A61B 6/032* (2013.01); *A61B 6/502* (2013.01); *G06T 11/006* (2013.01); *A61B 6/4405* (2013.01); *A61B 6/4411* (2013.01); *A61B 6/4429* (2013.01); *A61B 6/5217* (2013.01); *A61B 6/582* (2013.01); *G01N 23/044* (2018.02); *G01N 23/046* (2013.01); *G06T 11/003* (2013.01); *G06T 2211/416* (2013.01)

(58) Field of Classification Search
CPC ......... A61B 6/025; A61B 6/032; A61B 6/582; A61B 6/502
See application file for complete search history.

(56) References Cited

U.S. PATENT DOCUMENTS 6,097,025 A * 8/2000 Modlin ................ G01N 21/253
                                                       250/205
6,633,626 B2 * 10/2003 Trotter ................... G01N 23/04
                                                          378/62

(Continued)

*Primary Examiner* — David P Porta
*Assistant Examiner* — Djura Malevic
(74) *Attorney, Agent, or Firm* — Ziegler IP Law Group, LLC

(57) ABSTRACT

The present disclosure relates to the field of a cabinet x-ray incorporating an x-ray tube, an x-ray detector, and an optical camera for the production of organic and non-organic images. The computing device receives data including video data from an optical camera, a laser detector, an infrared detector, an ultrasonic detector, or a weight scale or pressure sensor, and determines automatically, based on the resultant data, if a sample/specimen has been left in the sample chamber. In particular, the disclosure relates to a system and method with corresponding apparatus for automatic detection if a sample/specimen has been left in the sample chamber without having to open the chamber door.

15 Claims, 9 Drawing Sheets

(51) Int. Cl.
*A61B 6/03* (2006.01)
*G06T 11/00* (2006.01)
*G01N 23/046* (2018.01)
*G01N 23/044* (2018.01)

(56) References Cited

U.S. PATENT DOCUMENTS

| | | | | |
|---|---|---|---|---|
| 6,922,246 B2* | 7/2005 | Nilson | ............... | A01K 1/031 |
| | | | | 250/458.1 |
| 7,113,217 B2* | 9/2006 | Nilson | ............... | A61B 5/0059 |
| | | | | 348/373 |
| 7,190,991 B2* | 3/2007 | Cable | ............... | A61B 8/4416 |
| | | | | 600/407 |
| 7,218,766 B2* | 5/2007 | Eberhard | ............... | A61B 6/463 |
| | | | | 128/922 |
| 7,474,399 B2* | 1/2009 | Nilson | ............... | G01N 21/6456 |
| | | | | 356/317 |
| 7,581,191 B2* | 8/2009 | Rice | ............... | A61B 5/0059 |
| | | | | 382/128 |
| 7,668,620 B2* | 2/2010 | Shoenfeld | ............... | G16H 20/13 |
| | | | | 700/237 |
| 9,138,193 B2* | 9/2015 | Lowe | ............... | A61B 6/035 |
| 9,347,894 B2* | 5/2016 | Sims | ............... | A61B 5/0071 |
| 9,642,581 B2* | 5/2017 | Lowe | ............... | A61B 6/5217 |
| 9,949,699 B2* | 4/2018 | Visser | ............... | A61B 6/566 |
| 10,557,786 B2* | 2/2020 | Gibbons | ............... | G01N 33/573 |
| 10,646,178 B2* | 5/2020 | Butani | ............... | A61B 8/4416 |
| 10,652,990 B2* | 5/2020 | Butani | ............... | A61B 6/467 |
| 10,670,545 B2* | 6/2020 | Butani | ............... | A61B 6/4435 |
| 10,830,712 B2* | 11/2020 | Butani | ............... | A61B 6/42 |
| 2003/0083756 A1* | 5/2003 | Hsiung | ............... | G05B 23/0286 |
| | | | | 700/28 |
| 2004/0059603 A1* | 3/2004 | Brown, Jr. | ............... | G16H 10/60 |
| | | | | 705/2 |
| 2004/0141588 A1* | 7/2004 | Francke | ............... | A61B 6/032 |
| | | | | 378/146 |
| 2006/0064000 A1* | 3/2006 | Vizard | ............... | A61B 6/4417 |
| | | | | 600/407 |
| 2006/0098773 A1* | 5/2006 | Peschmann | ............... | G01N 23/04 |
| | | | | 378/57 |
| 2007/0213617 A1* | 9/2007 | Berman | ............... | A61B 5/0091 |
| | | | | 600/473 |
| 2007/0238957 A1* | 10/2007 | Yared | ............... | A61B 5/0035 |
| | | | | 600/407 |
| 2012/0309636 A1* | 12/2012 | Gibbons | ............... | C12Q 1/52 |
| | | | | 506/9 |
| 2015/0131773 A1* | 5/2015 | Lowe | ............... | A61B 6/4429 |
| | | | | 378/5 |
| 2015/0131778 A1* | 5/2015 | Lowe | ............... | G01N 23/046 |
| | | | | 378/37 |
| 2015/0185234 A1* | 7/2015 | Gibbons | ............... | G01N 21/51 |
| | | | | 506/9 |
| 2015/0221091 A1* | 8/2015 | Sugiyama | ............... | A61B 5/5261 |
| | | | | 382/131 |
| 2016/0047834 A1* | 2/2016 | Nugent | ............... | G01N 21/51 |
| | | | | 435/2 |
| 2016/0334403 A1* | 11/2016 | Gibbons | ............... | C12Q 1/48 |
| 2017/0336706 A1* | 11/2017 | Wang | ............... | G01N 33/4833 |
| 2018/0275076 A1* | 9/2018 | Butani | ............... | G01N 23/044 |
| 2020/0320814 A1* | 10/2020 | Hastings | ............... | G07C 9/28 |

* cited by examiner

Typical Example of an X-ray Cabinet System

View in Sample Chamber with Door Open with
X-ray source at position (14) Top Center

**Lateral View of X-Ray Source
Mounted to Swing Arm at position (14)

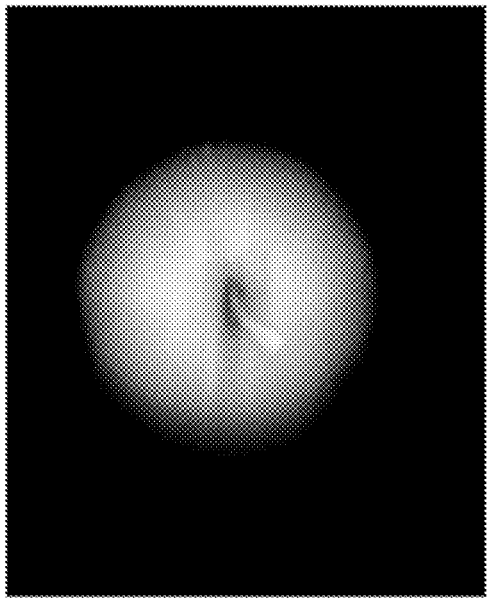
Fig. 7A - Top Slice – 59m
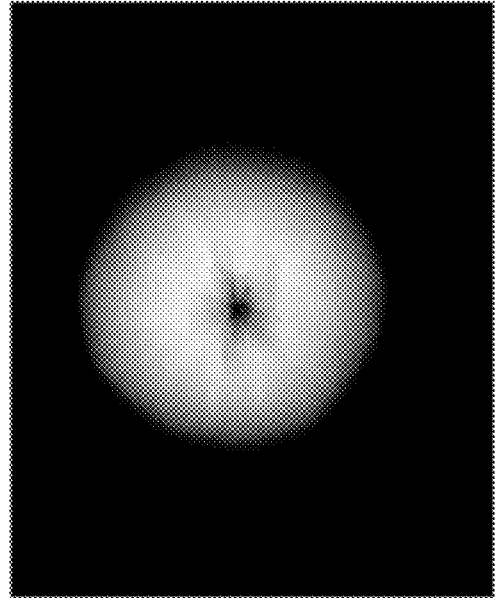
Fig. 7B - Bottom Slice – 13.5 mm
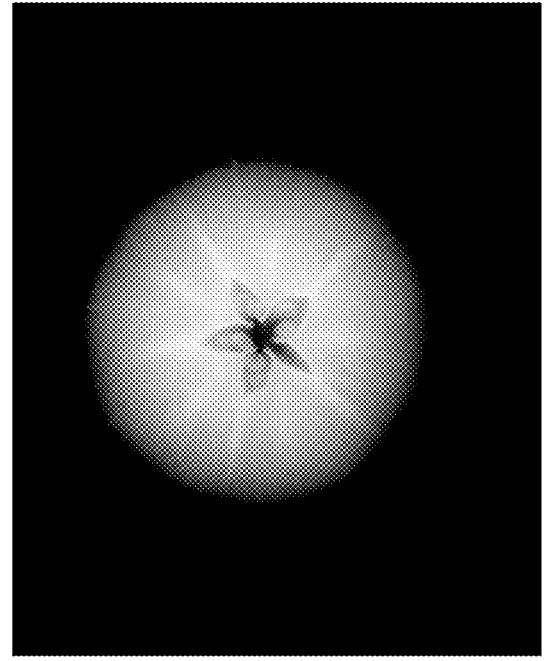
Fig. 7C - Middle Slice – 30.5 mm

SYSTEM AND METHOD FOR CABINET X-RAY SYSTEMS WITH AUTOMATIC SPECIMEN/SAMPLE ALERT

CROSS-REFERENCE TO RELATED APPLICATIONS

This application claims priority to and the benefit of U.S. Provisional Patent Application Ser. No. 62/546,338 filed Aug. 16, 2017, the disclosure of which is incorporated herein by reference in its entirety.

BACKGROUND

Field of the Present Disclosure

The present disclosure relates to the field of a cabinet x-ray incorporating a system and method for detecting automatically if a sample/specimen has been left in the sample chamber and displaying a message on the system monitor.

Background

It would be advantageous for a cabinet x-ray system to be able to automatically detect if the user has left a sample/specimen in the sample chamber after collecting a radiographic image.

When detected, a message could be displayed on the system monitor alerting the operator that something has been left in the sample chamber and will not allow them to proceed further until such sample is removed and the system reset.

DESCRIPTION OF THE RELATED ART

In general, this disclosure may enable a device (cabinet x-ray system) utilizing a computer to automatically alert the user if something has been left in the sample chamber after collecting a radiographic image.

During surgery, a breast specimen can be excised and the resulting tissue is imaged utilizing a cabinet x-ray system. With the frenzy of the surgery center, there are times when the specimen may be left in the cabinet x-ray. It would be advantageous for an alarm and/or visual indication that the specimen has not been removed from the cabinet x-ray unit and, for example, needs to be sent to pathology.

SUMMARY

The present disclosure relates to the field of a cabinet x-ray incorporating an x-ray tube, and an x-ray detector for the production of organic and non-organic images. The computing device receives data from an optical camera or other sensor and detector devices incorporated into the cabinet and determines, based on the resultant data, within a set timeframe, if a sample/specimen has been left in the cabinet including after a radiographic image has been attained. In particular, the disclosure relates to a system and method with corresponding apparatus for detecting if something has been left in the cabinet and displaying a message on the computing device and/or activating an audio prompt (e.g., an alarm sound) communicating that error.

In one embodiment, the aspects of the present disclosure are directed to a cabinet X-ray system for obtaining X-ray images of a specimen. The embodiment includes a cabinet defining an interior chamber, a display, an X-ray system, a controller and at least one sample detector. The X-ray system includes an X-ray source, an X-ray detector and a specimen platform. The at least one sample detector is to determine the presence or absence of the specimen disposed on the specimen platform. The controller is configured to receive a first set of data from the at least one sample detector before the specimen is disposed on the specimen platform; selectively energize the X-ray source to emit X-rays through the specimen disposed on the specimen platform to the X-ray detector; control the X-ray detector to collect a projection X-ray image of the specimen when the X-ray source is energized; selectively display the X-ray image on the display; receive a second set of data from the at least one sample detector after the X-ray detector has collected a projection X-ray image of the specimen; and compare the first set of data from the at least one sample detector to the second set of data from the at least one sample detector to determine if the specimen is disposed on the specimen platform.

In another embodiment, the aspects of the present disclosure are directed to a cabinet X-ray system for obtaining X-ray images, projection X-ray images and reconstructed tomosynthetic X-ray images of a specimen. The system includes a cabinet defining an interior chamber and an equipment enclosure, a display, an X-ray system, at least one sample detector and a controller. The X-ray system includes an X-ray source positioned in the interior chamber; an X-ray detector positioned in the interior chamber; a specimen platform positioned in the interior chamber and which is a protective cover of and in physical contact with the X-ray detector; and a motion control mechanism positioned in the interior chamber and configured for moving the X-ray source to or along a plurality of positions within the interior chamber relative to the specimen disposed on the specimen platform. The at least one sample detector is positioned in the interior chamber configured to determine the presence or absence of the specimen disposed on the specimen platform. The controller is positioned in the equipment enclosure and configured to receive a first set of data from the at least one sample detector before the specimen is disposed on the specimen platform; selectively energize the X-ray source to emit X-rays through the specimen to the X-ray detector at selected positions of the X-ray source relative to the specimen such that the isocenter of the emitted X-rays at the selected positions is located at a surface of the X-ray detector; control the X-ray detector to collect projection X-ray images of the specimen when the X-ray source is energized at the selected positions, wherein one of the projection X-ray images is a two-dimensional X-ray image taken at standard imaging angle of approximately 0°; create a tomosynthetic X-ray image reconstructed from a collection of projection X-ray images; process the collection of the projection X-ray images in the controller into one or more reconstructed tomosynthetic X-ray images representing a volume of the specimen and relating to one or more image planes that are selectively the same or different from that of the two-dimensional X-ray image; selectively display at least one of the two-dimensional X-ray image, the one or more reconstructed tomosynthetic X-ray images and the optical image on the display; receive a second set of data from the at least one sample detector after the X-ray detector has collected the projection X-ray images of the specimen; and compare the first set of data from the sample detector to the second set of data from the sample detector to determine if the specimen is disposed on the specimen platform.

In another embodiment, the aspects of the present disclosure are directed to a method for obtaining an X-ray image and detecting a specimen in a cabinet X-ray system. The cabinet X-ray image system includes cabinet defining an interior chamber, a display, an X-ray system, a controller and at least one sample detector. The X-ray system includes an X-ray source, an X-ray detector and a specimen platform. The at least one sample detector is to determine the presence or absence of the specimen disposed on the specimen platform. The controller is configured to receive a first set of data from the at least one sample detector before the specimen is disposed on the specimen platform; selectively energize the X-ray source to emit X-rays through the specimen disposed on the specimen platform to the X-ray detector; control the X-ray detector to collect a projection X-ray image of the specimen when the X-ray source is energized; selectively display the X-ray image on the display; receive a second set of data from the at least one sample detector after the X-ray detector has collected a projection X-ray image of the specimen; and compare the first set of data from the at least one sample detector to the second set of data from the at least one sample detector to determine if the specimen is disposed on the specimen platform. The embodiment includes generating a first set of data from the at least one sample detector before the specimen is disposed on the specimen platform; controlling the X-ray detector to collect an X-ray image of the specimen when the X-ray source is energized; generating a second set of data from the at least one sample detector after the X-ray detector has collected an X-ray image of the specimen; and comparing the first set of data from the at least one sample detector to the second set of data from the at least one sample detector to determine if the specimen is disposed on the specimen platform.

BRIEF DESCRIPTION OF THE DRAWINGS

To further clarify the above and other advantages and features of the present disclosure, a more particular description of the disclosure will be rendered by reference to specific embodiments thereof that are illustrated in the appended drawings. It is appreciated that these drawings depict only typical embodiments of the disclosure and are therefore not to be considered limiting of its scope. The disclosure will be described and explained with additional specificity and detail through the use of the accompanying drawings in which:

FIGS. 7A, 7B and 7C—Displays the results of the imaging of an apple at multiple depth cuts after tomosynthesis reconstruction in a cabinet X-ray system incorporating aspects of the present disclosure.

DETAILED DESCRIPTION OF EMBODIMENT

Figure 1:
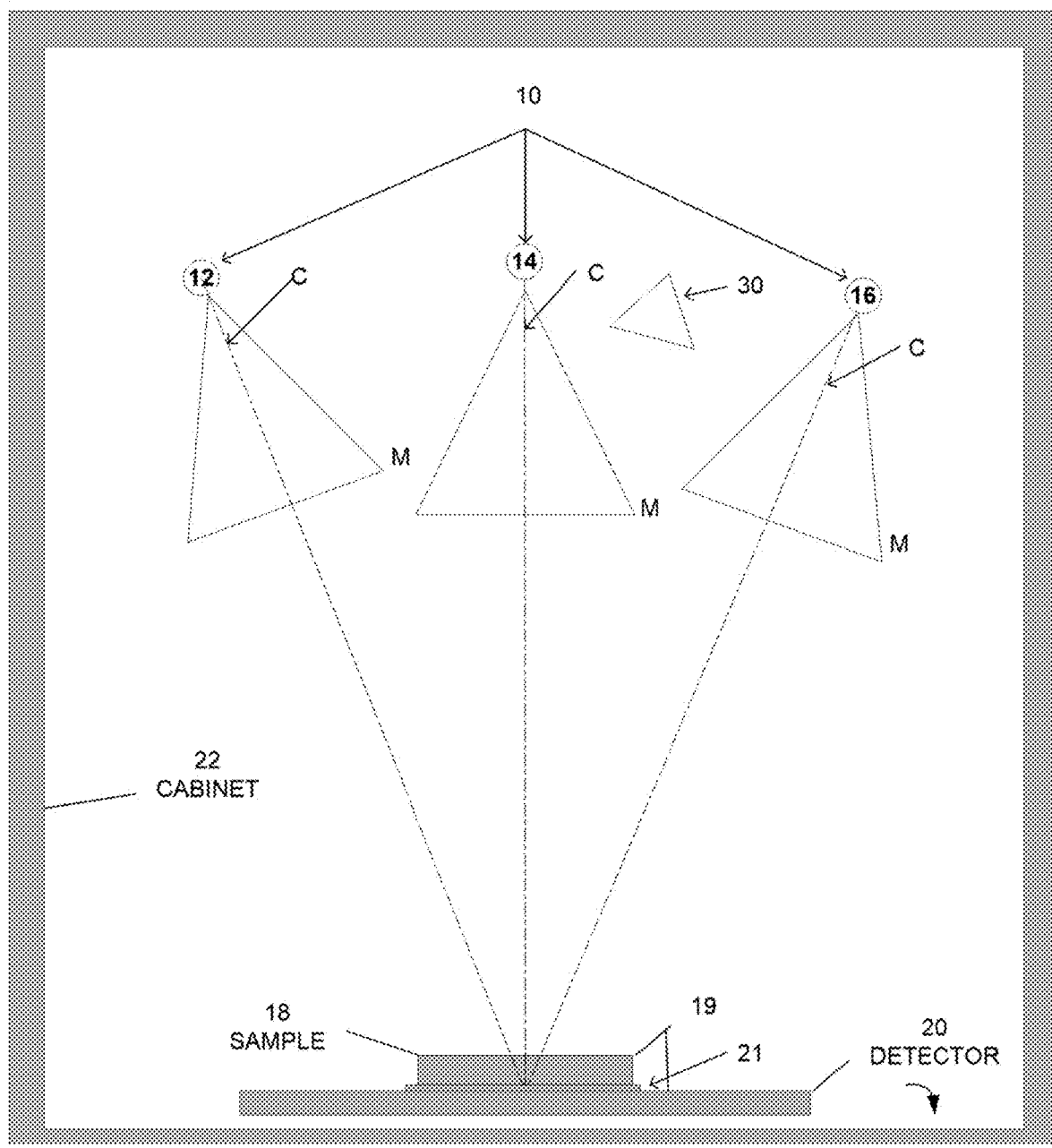
FIG. 1—Schematically illustrates a front view of an X-ray source, a specimen/sample, and a digital detector, where the X-ray source moves relative to the specimen for imaging the specimen at different angles, in one embodiment of a system incorporating aspects of the present disclosure.

Reference will now be made to figures wherein like structures will be provided with like reference designations. It is understood that the drawings are diagrammatic and schematic representations of exemplary embodiments of the disclosure and are not limiting of the present disclosure nor are they necessarily drawn to scale.

In general, aspects of this disclosure include a device (cabinet x-ray system) utilizing a sample detector sensor to determine the presence of a sample/specimen in the device beyond a given length of time, including after an X-ray image has been obtained. The purpose is to alert the staff tending to or in proximity to the device that the sample/specimen has been left in the device and needs to be removed. The X-ray image can include a two-dimensional (2-D) X-ray image or a synthetic X-ray image assembled from more than one X-ray image (e.g., a tomosynthetic image).

The present disclosure and embodiments included therein can relate to specimen radiography but the disclosure is not isolated to specimen radiography but may be utilized, for example, for non-destructive testing, pathology as well as any radiographic analysis of organic and non-organic samples or specimens, requiring examination by a cabinet x-ray system. The sample detector sensor is intended to detect the presence of the sample/specimen and can be, for example, a camera (for example, an HD camera), a laser detector, an infrared detector, an ultrasonic detector or a pressure sensor or weight scale on which the sample/specimen rests (for example, in a sample/specimen tray), capable of fitting within the confines of the cabinet x-ray system.

One embodiment of the present disclosure includes an optical camera (e.g., an HD camera) imaging or other sensor (e.g., laser sensor, an infrared sensor, an ultrasonic sensor) detecting in direction of and substantially an unimpeded view of the center of the sample chamber in a cabinet x-ray unit or includes a pressure sensor or weight scale in concert with the sample tray or platform where a sample/specimen would be positioned is capable of detecting the sample/specimen positioned therein in a cabinet x-ray unit. This image or presence of a detected object in the area upon which the camera or other sensor is aimed or positioned would then be compared after a given amount of time with an earlier image or record acquired at the start of the system during calibration before the sample/specimen is positioned in the cabinet X-ray unit, using software included in the computer controlling the cabinet X-ray unit. The computer would compute within a set time frame if an object has been left in the sample chamber after a radiographic image has been taken or at shutdown of the device. It can be appreciated that a laser, infrared or ultrasonic detector, or a weight sensing device (e.g., a scale) or pressure sensor incorporated into the specimen tray may be utilized in the place of an optical camera.

The embodiments as related herein explain how they would relate to biological or medical sample/specimen radiography but the disclosure is not isolated to biological or medical sample/specimen radiography and may be utilized for non-destructive testing, pathology as well as any radiographic analysis of any sample/specimen, organic and non-organic, requiring a cabinet x-ray system and the sample detector is not limited to just an optical camera but to any device fitting within the confines of the cabinet x-ray system that could detect if a sample/specimen has been left in the sample chamber, for example, after an image has been taken or when the device is being shut down, for example, delaying or preventing device shutdown until the sample/specimen has been removed from the sample chamber.

Reference will now be made to figures wherein like structures will be provided with like reference designations. It is understood that the drawings are diagrammatic and schematic representations of exemplary embodiments of the disclosure and are not limiting of the present disclosure nor are they necessarily drawn to scale. FIGS. 1-9 depict various features and uses of embodiments of the present disclosure, which embodiments are generally directed to a system that can utilize an optical camera, preferably an HD or similar real-time camera, to capture an image of the specimen/sample before, concurrently with or after the acquisition of an x-ray image.

The systems and methods of embodiments of the present disclosure also address unmet needs by providing 2-D x-ray imaging and tomosynthesis apparatus and techniques that include optical imaging for imaging breast specimens that overcome the shortfall of the data received from two-dimensional and tomosynthesis imaging systems alone. The aspects of embodiments of the present disclosure also enable the use of tomosynthesis to efficiently provide accurate three-dimensional imaging of a specimen in which overlapping images having differing attenuation characteristics can be obtained by applying a three-dimensional reconstruction algorithm all in an x-ray cabinet system.

As used herein, the term "computer," "computer system", or "processor" refers to any suitable device operable to accept input, process the input according to predefined rules, and produce output, including, for example, a server, workstation, personal computer, network computer, wireless telephone, personal digital assistant, one or more microprocessors within these or other devices, or any other suitable processing device with accessible memory.

The term "computer program" or "software" refers to any non-transitory machine-readable instructions, program or library of routines capable of executing on a computer or computer system including computer readable program code.

Digital breast specimen tomosynthesis is disclosed in U.S. Pat. No. 2015/0131773 (U.S. Pat. No. 9,138,193), Lowe, et al., entitled "SPECIMEN RADIOGRAPHY WITH TOMOSYNTHESIS IN A CABINET," the disclosure of which is hereby incorporated by reference in its entirety.

The term "sample detector" refers to an apparatus that can ascertain the presence or absence of a sample/specimen in a specimen tray or on specimen platform of a cabinet X-ray device and can include a camera including an optical camera, an infrared detector, a laser detector, an ultrasonic detector, a weight scale or a pressure sensor.

The terms "camera" or "optical camera" refer to an instrument, including an optical instrument for capturing images in black and white, gray scale or color (preferably color), ultrasonic, or laser using reflected and/or emitted wavelengths of the electromagnetic spectrum, for example, visible light, infrared or fluorescent light, from an object, similar to a photograph or that which could be viewed by a human eye, using an electronic light-sensitive sensor array. These terms may include such instruments producing images in standard resolution or HD as well as a digital camera that can directly capture and store an image in computer-readable form using an array of electronic light-sensitive elements—typically semiconductor photo-sensors—that produce a light-intensity-dependent electronic signal in response to being illuminated.

For some embodiments using a laser, infrared or ultrasonic detector (including imaging thereby), the apparatus includes a laser, infrared or ultrasonic sensor (including a laser, infrared or ultrasound sensor array) and a laser, infrared or ultrasonic emitter separately mounted within the cabinet or in combination in a common housing. The laser, infrared or ultrasonic emitter generates the laser, infrared or ultrasonic energy that is aimed at the sample/specimen and reflects off of it, the reflected laser, infrared or ultrasonic energy that is reflected then being sensed by the laser, infrared or ultrasonic sensor and generating a data signal that is sent to a computer.

Reference will now be made to figures wherein like structures will be provided with like reference designations. It is understood that the drawings are diagrammatic and schematic representations of exemplary embodiments of the disclosure and are not limiting of the present disclosure nor are they necessarily drawn to scale.

Specimen tomography is a three-dimensional specimen imaging system. It involves acquiring images of a sample at multiple viewpoints, typically over an arc or linear path. The three-dimensional image is constructed by the reconstruction of the multiple image data set.

One embodiment of a system 100 incorporating aspects of the present disclosure is illustrated in FIG. 1 The system 100 is totally enclosed or housed in an X-ray cabinet 22. In accordance with the aspects of the disclosed embodiments, the X-ray source 10 moves around the stationary sample, 18, typically, but not necessarily, in an arc. References 12, 14, and 16 of FIG. 1 illustrate exemplary positions of the X-ray source 10 within the X-ray cabinet 22. The reference "C" at each of the positions 12, 14, 16 of the X-ray source 10 in FIG. 1 refers to the point source of the X-ray beam. The reference "M" refers to the spread or fan of the X-ray beam. A sample detector 30 including, for example, a laser detector, an infrared detector, a camera or an ultrasonic detector, detects if there is a specimen 18 present in the chamber 22.

The sample detector 30 is positioned to detect toward the center of the sample chamber or the specimen platform 19 where a sample/specimen would be positioned. The sample detector 30 can detect the presence or absence of a sample/specimen and sends such signal, visual or image data generated to computer 470 to which it connected. The sample detector 30 can transmit data (including image data or signal data from the reflected energy received by the detector's associated sensor) to the computer 470 before the sample/specimen is positioned for X-ray imaging and after the sample/specimen is positioned for X-ray imaging to provide the computer with information to determine if there is a difference in the data from before the sample/specimen is positioned to after indicating that the sample/specimen is present in the sample chamber.

While the X-ray detector 20 may move or rotate, in accordance with one aspect of the present disclosure, the X-ray detector 20 remains stationary relative to the sample 18 and X-ray source 10 to maintain an equidistant center point. The X-ray data taken at each of a number of exemplary positions 12, 14, 16 of the X-ray source 10 relative to the sample 18 within the X-ray cabinet 22 is processed to form images, where two or more of the differing image positions are utilized to form a digital tomosynthesis image.

In one embodiment, the aspects of the present disclosure limit the arc or linear travel of the x-ray source 10 over about a 20° to about a 50° arc, preferable about 30°, more preferable 20°. The movement can be clockwise or counter clockwise along a path, which includes for example, one or more, or a combination thereof, of the following exemplary ranges: between approximately 350° (reference position 12) to 0° (reference position 14) to 10° (reference position 16), or between approximately 340° (reference position 12) to 0° (reference position 14) to 20° (reference position 16) and or between approximately 335° (reference position 12) to 0° (reference position 14) to 25° (reference position 16). The ranges recited herein are intended to be approximate and inclusive of start and endpoints. In the example of FIG. 1 the X-ray detector 20 is stationary as is the sample 18. The sample 18 also referred to as the "object" or "imaging object" is disposed on or rests on the specimen platform 19 (which is a protective cover).

Figure 2:
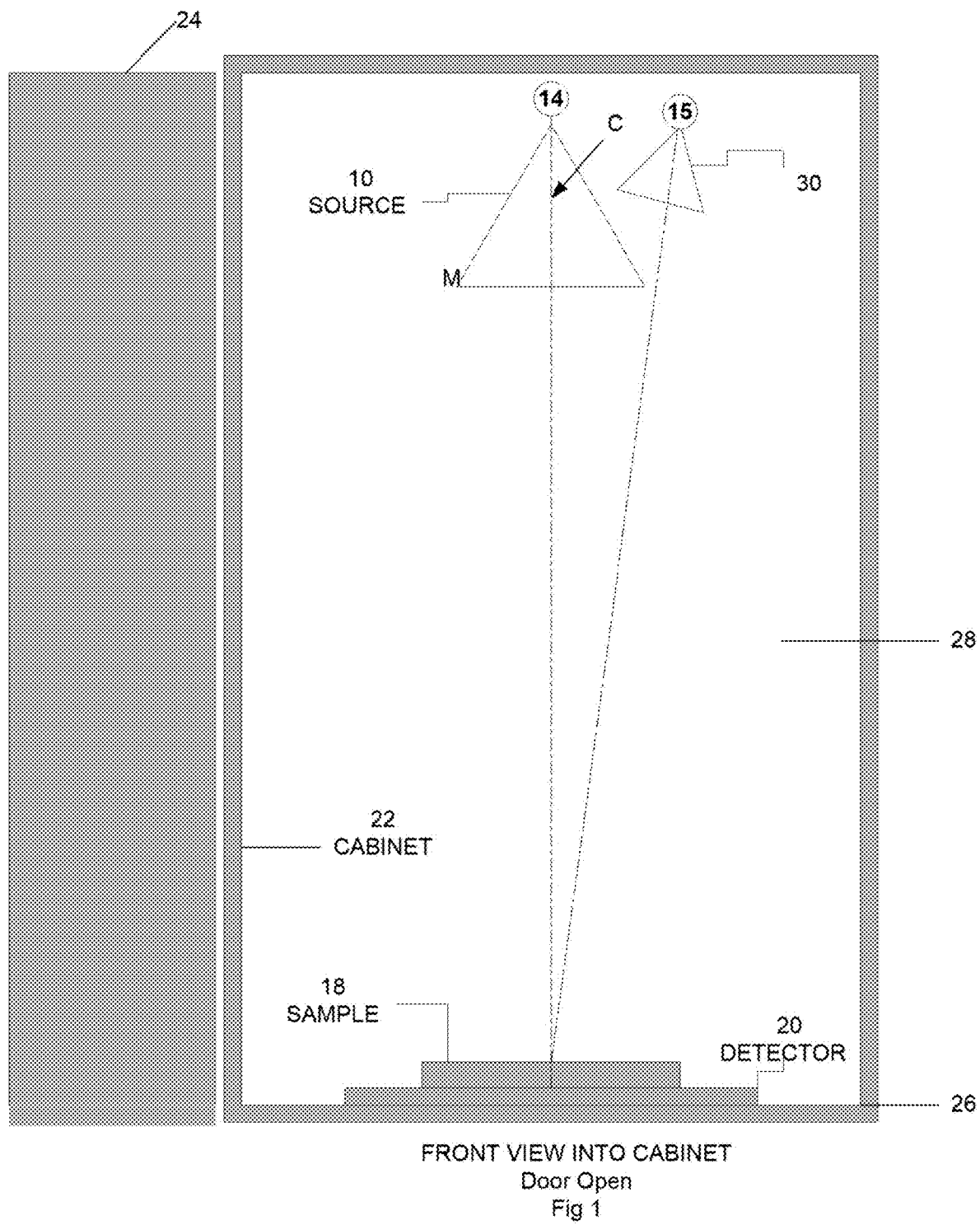
FIG. 2—Schematically illustrates an exemplary orientation of the X-ray source, specimen, and digital detector as viewed when the door of the cabinet is open, in one embodiment of a system incorporating aspects of the present disclosure.
Figure 5:
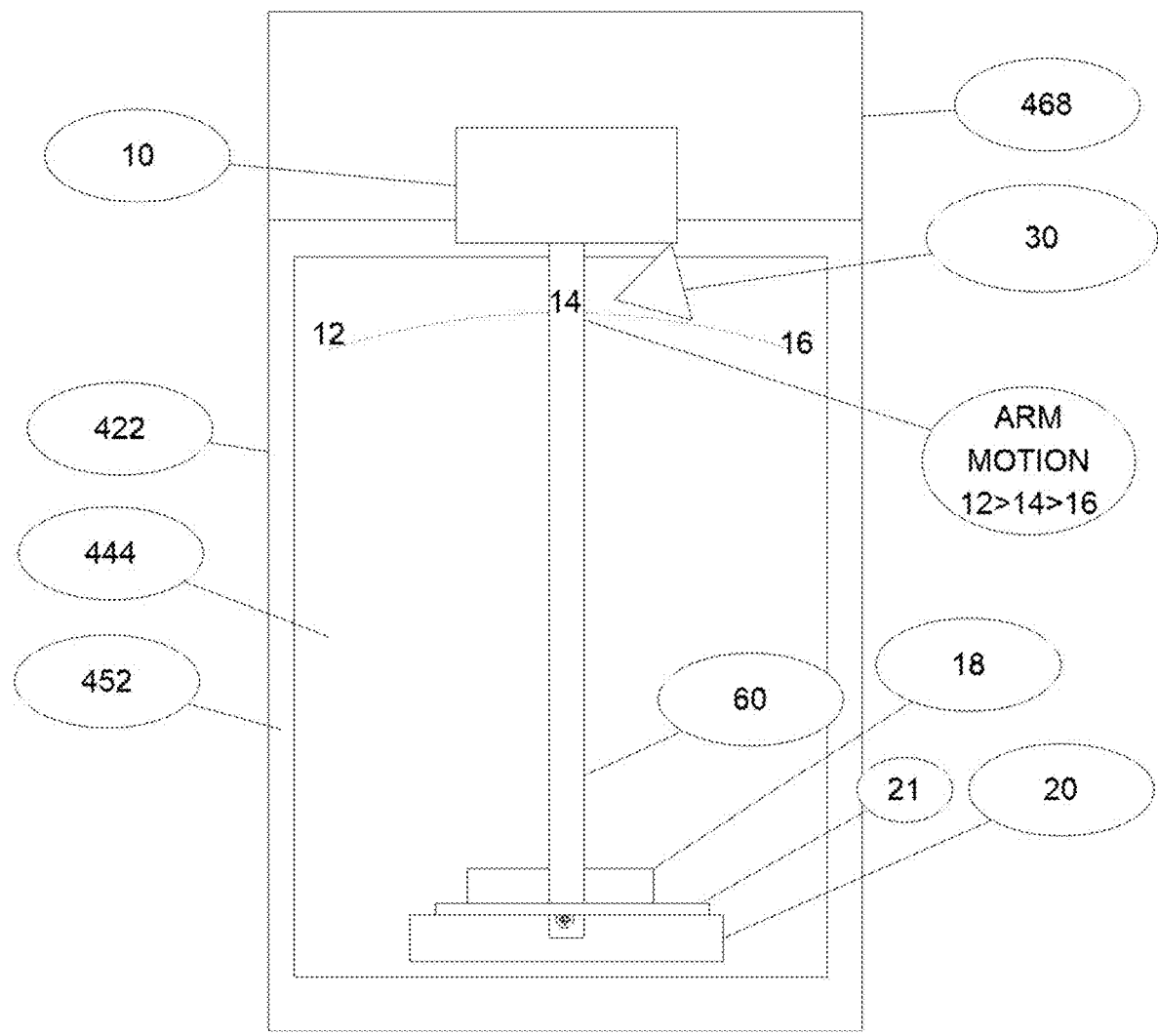
FIG. 5—Displays the sample chamber of the embodiment of FIG. 4 with the swing arm and a detector.

Sample detector 30 is included in FIGS. 1 2 and 5 as well showing embodiments in sample detector 30, for example, located at position 15 in the cabinet x-ray unit such that it is capable of capturing a visual image or data of sample 18 in cabinet 22 and x-ray cabinet chamber 28 in FIGS. 1 and 2 and in cabinet 422 and sample chamber 444 in FIG. 5

In other embodiments of the present disclosure, a second sample detector 21 that may be proximal to the specimen platform 19 or incorporated separately or in conjunction with X-ray detector 20. The second sample detector 21 may include, for example, a weight scale sensor, a pressure sensor or a strain gauge, on which the sample/specimen rests, directly or, as in the FIG. 1 embodiment, indirectly using a specimen platform (that can include a sample tray) and the resultant data or signal from the second sample detector may be transmitted to the computer 470 to signal whether a sample is sitting on the platform 19 or other surface of the X-ray detector 20. The second sample detector 21 can detect the presence or absence of a sample/specimen using the sensed or detected mass or weight of the sample/specimen. The second sample detector can transmit data to the computer 470 before the sample/specimen is positioned for X-ray imaging and after the sample/specimen is positioned for X-ray imaging to provide the computer 470 with information to determine if there is a difference in weight from before the sample/specimen is positioned to after indicating that the sample/specimen is present in the sample chamber.

Embodiments of the present disclosure can include one or both of the sample detector and the second sample detector.

In operation, source 10 is energized to emit an x-ray beam, generally throughout its travel along one or more of the paths or positions described above. The x-ray beam travels through the sample 18 to the X-ray detector 20 and the multiple images collected at varying angles are stored and then utilized for the tomosynthesis reconstruction. The X-ray source 10 may range from about 0 kVp to about 90 kVp, preferably a 50 kVp 1000 μa X-ray source.

Different embodiments of the present disclosure can utilize different ranges of motion of one or more of the X-ray source 10 and X-ray detector 20 as well as changing the angularity of one or both. The inventive aspects of the present disclosure differ from the prior art in that in prior art systems either the detector and X-ray source 10 and/or the isocenter is above the sample and not at the detector surface. In accordance with the aspects of the present disclosure, in one embodiment, the X-ray source 10 is configured to move, as described herein, while the detector is configured to remain stationary or in a fixed position.

The X-ray detector 20 and associated electronics generate image data in digital form for each pixel at each of the angular positions, 12, 14, 16 of X-ray source 10 and translations positions of the X-ray detector 20 relative to the sample 18. While only three positions 12, 14, 16 are illustrated in FIG. 1, in practice more images are taken at differing angles. For example, in one embodiment, images can be taken at approximately every 1° of rotation or motion of source 10. The camera 30 represented in the figure may capture an optical image, preferably an HD image of the sample which can be stored with the radiographic images in computer 470.

FIG. 2 schematically illustrates one embodiment of the orientation of the X-ray source 10 as seen when the door 24 is opened and the X-ray source 10 is locate at approximately 0°, reference point 14 in this example, within the X-ray cabinet 22. In this embodiment, the motion of the X-ray source 10 can generally occur from the back to the front of the X-ray cabinet 22 with the X-ray detector 20 oriented, or otherwise disposed, at the base 26 of the X-ray cabinet 22, within the X-ray cabinet chamber 28. In one embodiment, the X-ray detector 20 is suitably coupled to the base 26 of the X-ray cabinet 22. The X-ray spread in this example can be from about 0 kVp to about 50 kVp with the system preferably utilizing an AEC (Automatic Exposure Control) to ascertain the optimal setting to image the object or sample 18 being examined.

In one embodiment, the X-ray detector 20, X-ray source 10, and the swing arm 60 (FIG. 5) servo mechanism as well as the sample detector and the second sample detector are controlled via a combination of one or more of software and hardware, such as non-transitory machine-readable instructions stored in a memory that are executable by one or more processors. On example of such a configuration can include controller cards of a computer 470 (FIG. 4), such as a MS Windows based computer. In one embodiment, non-transitory machine readable instructions being executed by one or more processors of the computer 470 is utilized to compile data received from the X-ray detector 20 and present resulting images to a suitable display or monitor 472 (FIG. 4) at each imaging position, such as positions 12, 14 and 16 shown in FIG. 1, the X-ray detector 20 generates the respective digital values for the pixels in a two-dimensional array. The size of X-ray detector 20 may range, for example, from about 5.08 centimeters by 5.08 centimeters to about 40.64 centimeters by 40.64 centimeters, preferably about 12.7 centimeters by 15.24 centimeters. In one example, X-ray detector 20 has a rectangular array of approximately 1536×1944 pixels with a pixel size of 74.8 micrometers. The image dataset attained at each respective position may be processed either at the full spatial resolution of X-ray detector 20 or at a lower spatial resolution by overlapping or binning a specified number of pixels in a single combined pixel value.

For example, if we bin at a 2×2 ratio, then there would be an effective spatial resolution of approximately 149.6 micrometers. This binning may be achieved within the original programming of the X-ray detector 20 or within the computer 470 providing the tomosynthetic compilation and image.

Such computer software and hardware including non-transitory machine readable instructions being executed by one or more processors of the computer 470 can also utilized to provide instructions to and collect and compile data received from the sample detector 30 and second sample detector 21 as well as utilize a clock incorporated into the computer 470 to, for example, countdown a predetermined amount of time between detector data generated before a sample/specimen is placed in the sample chamber and generated after an X-ray image or images is/are taken. The computer software and hardware including non-transitory machine readable instructions including image comparison software can also be used to compare the two sets of detector data to see if there is any difference between the two, a difference indicating that the sample/specimen remains in the sample chamber.

Figure 3:
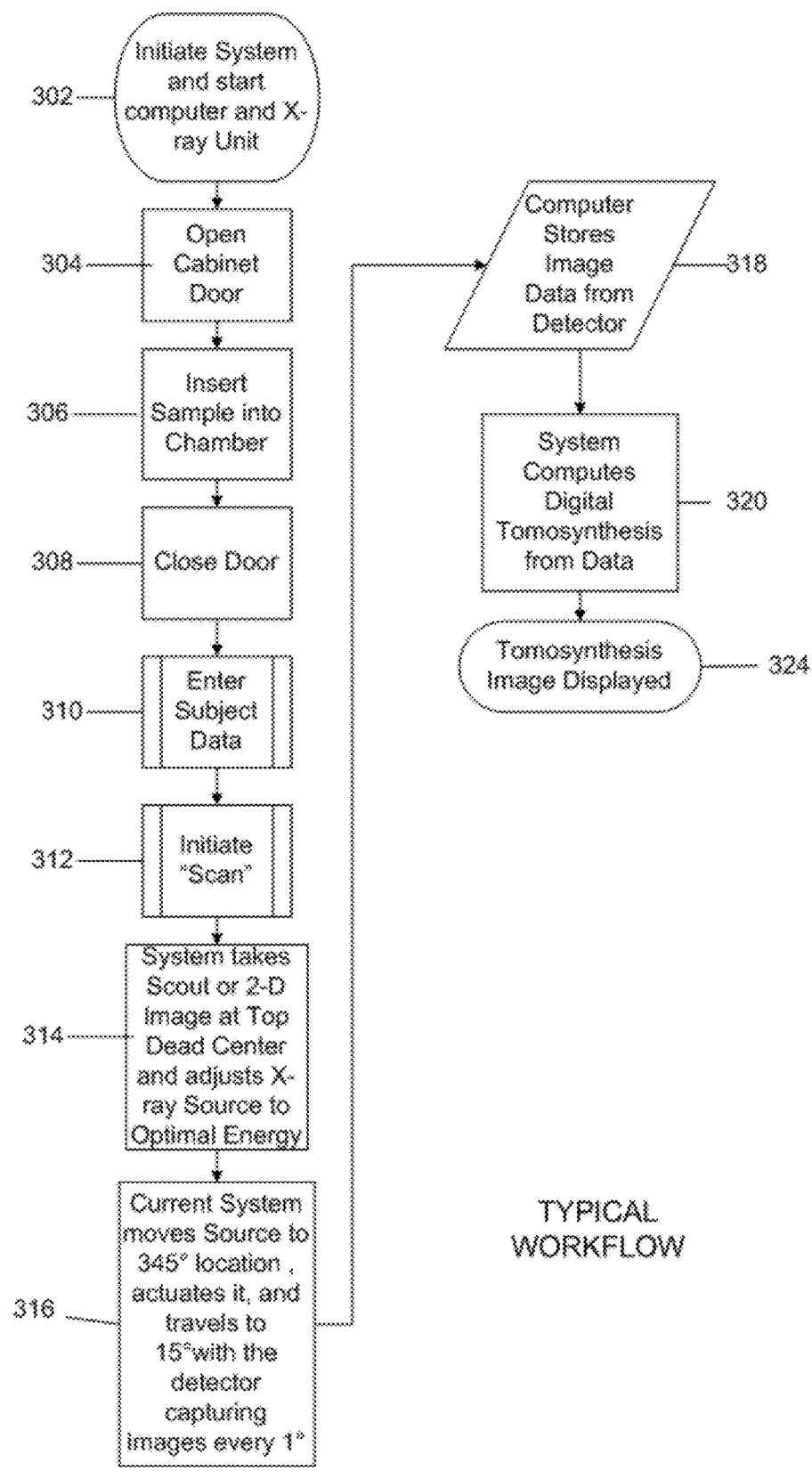
FIG. 3—Displays an exemplary workflow/flowchart of an aspect of the disclosed embodiments.

FIG. 3 illustrates one embodiment of an exemplary workflow from initiating 302 the system 100 through imaging, reconstruction and display 324 of data images collected of the sample 18.

As will be generally understood, the system 100 is initiated 302, the X-ray cabinet door 24 opened 304, and the sample 18 placed into 306 the X-ray cabinet chamber 28. As shown in FIG. 2, for example, the sample 18 is positioned on the X-ray detector 20 in a suitable manner. The door 24 is closed 308.

The data and information regarding the sample 18, including any other suitable information or settings relevant to the imaging process and procedure, is entered 310 into the computer 470. The scan is initiated 312. The system 100 will take 314 scout or 2-D images at Top Dead Center, which for purposes of this example is position 14 of FIGS. 1 and 2. The X-ray source 10 can then be moved to other positions, such as positions 12 and 16, and the X-ray detector 20 can be used to capture 316 images at various increments along the travel path of the X-ray source 10, such as about every 1 degree.

The captured images are stored 318 and digital tomosynthesis is performed 320. The tomosynthesis image is then displayed 324.

Other embodiments of a system 100 incorporating aspects of the present disclosure are illustrated in FIGS. 1 and 2 where system 100 is totally enclosed or housed in an x-ray cabinet 22 and the x-ray source 10 is stationary relative to the stationary sample, 18 and can be used to obtain a 2-D image. In these embodiments, x-ray source 10 can be positioned at position 14 and the reference "C" refers to the point source of the x-ray beam and the reference "M" refers to the spread or fan of the x-ray beam. While the X-ray detector 20 may move or rotate, in accordance with one aspect of the present disclosure, the X-ray detector 20 can remain stationary relative to the sample 18 and x-ray source 10 to maintain an equidistant center point. The sample 18 also referred to as the "object" or "imaging object" may be disposed on or rest on the specimen platform 19 (which is a protective cover) or other surface of the X-ray detector 20. As with the previous embodiments described herein, the inventive aspects of the present disclosure differ from the prior art in that in prior art systems either the detector and x-ray source 10 and/or the isocenter is above the sample and not at the detector surface. In operation, source 10 is energized to emit an x-ray beam at position 14, located at approximately 0°, and thereby obtain a 2-D image of sample 18. In operation, source 10 is energized to emit an x-ray beam, generally throughout its travel along one or more of the paths or positions described above. The x-ray beam travels through the sample 18 to the detector 16 and a 2-D image is stored. The x-ray source 10 may range from about 0 kVp to about 90 kVp, preferably a 50 kVp 1000 µa x-ray source.

Figure 4:
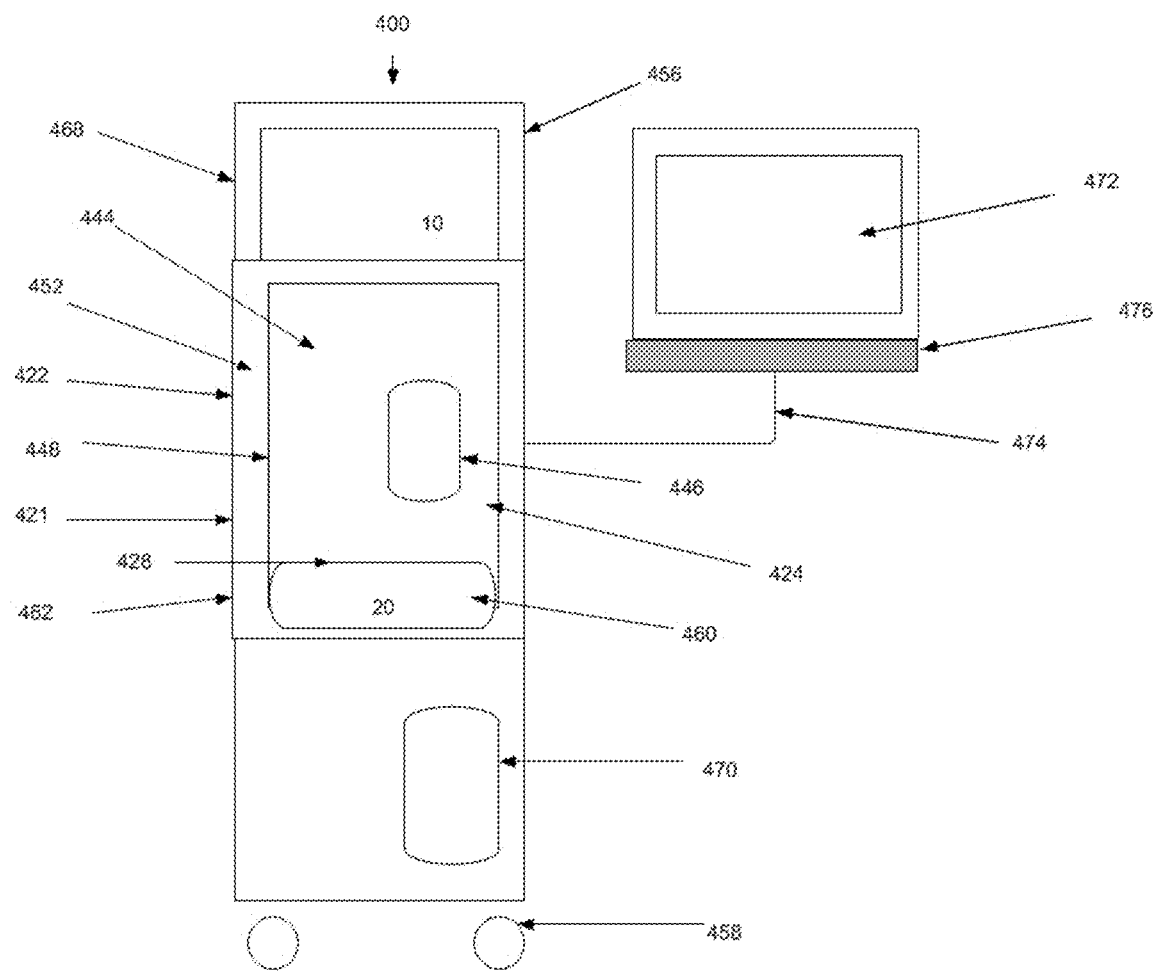
FIG. 4—Displays an example of an X-ray Cabinet System incorporating aspects of the present disclosure.

FIG. 4 shows one embodiment of an X-ray Cabinet System 400 incorporating aspects of the present disclosure. In this embodiment, the X-ray Cabinet System 400 is mounted on wheels 458 to allow easy portability. In alternate embodiments, the X-ray Cabinet System 400 can be mounted on any suitable base or transport mechanism. The cabinet 422 in this example, similar to the exemplary X-ray cabinet 22 of FIG. 1, is constructed of a suitable material such as steel. In one embodiment, the cabinet 422 comprises painted steel defining a walled enclosure with an opening or cabinet chamber 428. Within the cabinet chamber 428, behind door 424, resides an interior space forming a sample chamber 444, which in this example is constructed of stainless steel. Access to the sample chamber 444 is via an opening 446. In one embodiment, the opening 446 of the sample chamber 444 has a suitable door or cover, such as a moveable cover 448. In one embodiment, the moveable cover 448 comprises a door which has a window of leaded glass.

Between the outer wall 421 of cabinet 422 and the sample chamber 444 are sheets of lead 452 that serve as shielding to reduce radiation leakage emitted from the X-ray source 10. In the example of FIG. 4, the X-ray source 10 is located in the upper part 456 of the cabinet 422 along with the sample detector (in embodiments using it to detect the presence of a sample/specimen), in the source enclosure 468. The X-ray detector 20 is housed in the detector enclosure 460 at an approximate midpoint 462 of the cabinet 422 along with the second sample detector (in embodiments using it to detect the presence of a sample/specimen).

Figure 6:
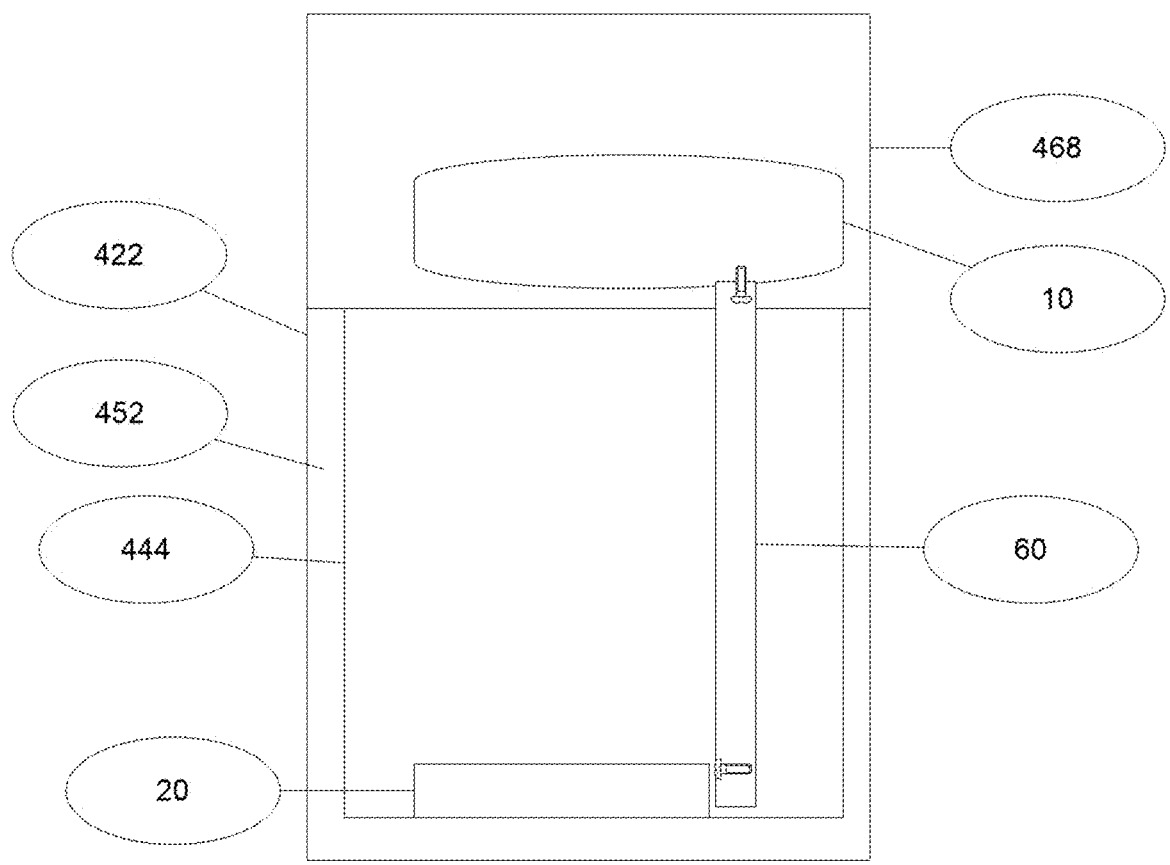
FIG. 6—Displays the lateral view of the X-ray source of the embodiment of FIG. 4 mounted to the top of the swing arm.

In one embodiment, a controller or computer 470 controls the collection of data from the X-ray detector 20, controls the collection of data from either or both of the sample detector and second sample detector, controls the swing arm 60 shown in FIGS. 5 & 6, and X-ray source 10. A monitor 472 displays the compiled data and can, for example, be mounted on an articulating arm 474 that is attached to the cabinet 422. The computer 470 receives commands and other input information entered by the operator via a user interface 476, such as a keyboard and mouse for example. In one embodiment, the computer 470 can comprise a touch screen or near touch screen device. Although the aspects of the disclosed embodiments will generally be described with respect to a computer 470, it will be understood that the computer 470 can comprise any suitable controller or computing device. Such computing devices can include, but are not limited to, laptop computers, mini computers, tablets and pad devices. Computer 470 is also connected electronically to at least one of the sample detector and second sample detector in order to control and receive data therefrom and monitor 472 can display error codes or notifications that a sample/specimen remains in the sample chamber and needs to be removed.

The computer 470 can be configured to communicate with the components of the X-ray cabinet system 400, including the sample detector and second sample detector, in any suitable manner, including hardwired and wireless communication. In one embodiment, the computer 470 can be configured to communicate over a network, such as a Local Area Network or the Internet.

FIG. 5 shows a front interior view and FIG. 6 shows a lateral interior view of the sample chamber of imaging unit cabinet of FIG. 4. In this embodiment, a sample 18 is placed or otherwise disposed onto the X-ray detector 20. Using the computer 470 shown in FIG. 4, the operator enters in the parameters for the scan via the user interface 476, which can be displayed on the monitor 472. As used herein, the term "display" or "monitor" means any type of device adapted to display information, including without limitation CRTs, LCDs, TFTs, plasma displays, LEDs, and fluorescent devices. The computer 470 then sends the appropriate commands to the X-ray source 10 and X-ray detector 20 to activate image collection while the swing arm 60 is moving along a path or arc from position 14 to 12 to 16 (which are shown in FIGS. 1 and 5) or vice versa as described, which in this embodiment are at 345°, 0°, and 15° respectively with 0° at top dead center. At the end of the travel of the swing arm 60 at either position 12 or 16, the computer 470 issues the command to the X-ray source 10 and the X-ray detector 20 to cease operating. The individual 2-dimensional (2-D) images which were collected, in this example at 1° increments, are then tabulated in the computer 470 to create the tomosynthetic images. In one embodiment, the operator may select which images they wish via the user interface 476 as they are being displayed on the monitor 472. In one embodiment, the devices and components of the X-ray cabinet system 400 are suitably communicatively coupled together, including one or more of hard wire connections or wireless connections using a suitable wireless connection and communication transmission protocol, as will generally be understood. The X-ray cabinet system 400 can also be configured to transfer images via USB, CD-ROM, or WIFI.

The dynamic imaging software of the disclosed embodiments reconstructs three-dimensional images (tomosynthesis) from two-dimensional projection images in real-time and on-demand. The software offers the ability to examine any slice depth, tilt the reconstruction plane for multiplanar views and gives higher resolution magnifications. FIGS. 7A, 7B, and 7C illustrate exemplary images of an apple using the above process.

FIG. 7A is an image of a slice of the apple at it's very top. 59 mm from the bottom. FIG. 7B is an image of an apple computed at 30.5 mm up from the detector, and FIG. 7C is a view of the apple computed at 13.5 mm from the bottom.

The real-time image reconstruction of the present disclosure enables immediate review, higher throughput, and more efficient interventional procedures reducing patient call backs and data storage needs. Multiplanar reconstruction enables reconstruction to any depth, magnification and plane, giving the viewer the greater ability to view and interrogate image data, thereby reducing the likelihood of missing small structures. Built-in filters allow higher in plane resolution and image quality during magnification for greater diagnostic confidence. Software is optimized for performance using GPU Technology.

The reconstruction software used in conjunction with the aspects of the present disclosure provides the users greater flexibility and improved visibility of the image data. It reconstructs images at any depth specified by the user rather than at fixed slice increments. With fixed slice increments, an object located between two reconstructed slices, such as a calcification, is blurred and can be potentially missed. The aspects of the present disclosure provide for positioning the reconstruction plane so that any object is exactly in focus. This includes objects that are oriented at an angle to the X-ray detector 20. The aspects of the present disclosure provide for the reconstruction plane to be angled with respect to the detector plane.

Embodiments of the present disclosure that include a device (cabinet x-ray system) utilizing the camera can also capture an optical image (in black and white, gray scale or color, preferably color), preferably in real-time, of a sample or specimen also being x-rayed to produce an x-ray image. The photo/captured camera optical image, preferably in real-time, may be displayed on the monitor.

Figure 8:
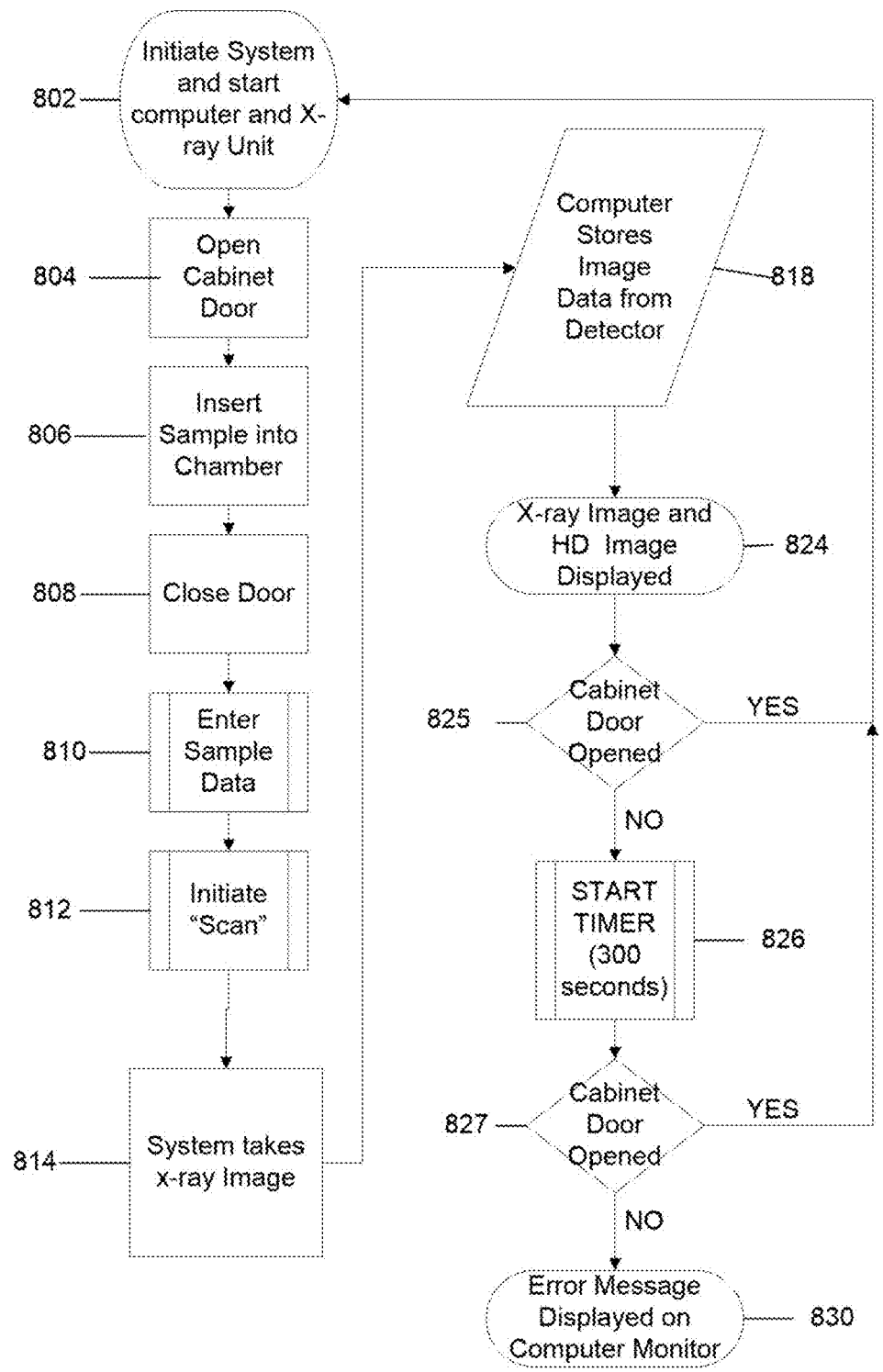
FIG. 8 is a display of the basic workflow of one embodiment of the present disclosure.
Figure 9:
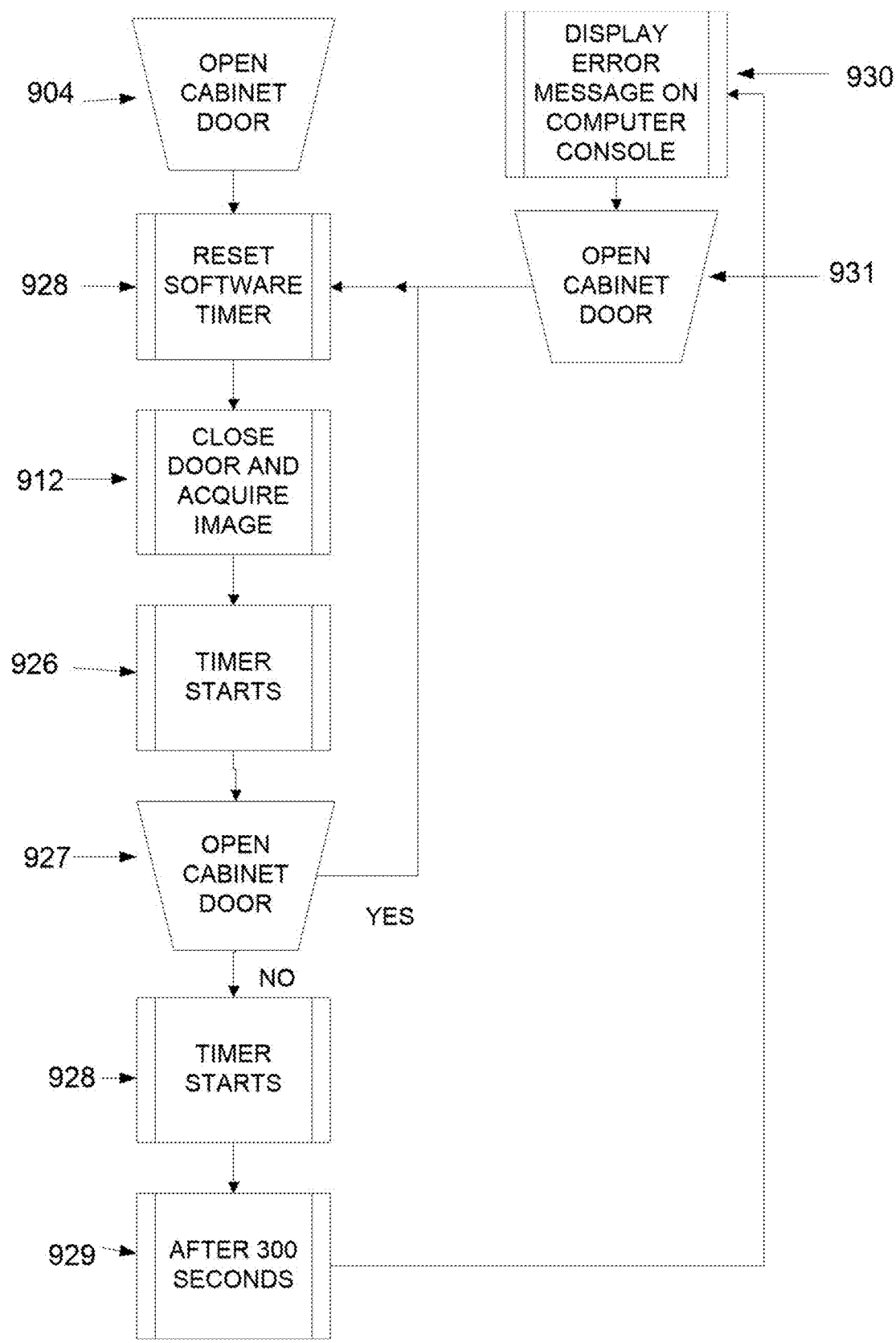
FIG. 9 is a display of the basic software logic workflow of another example embodiment of the present disclosure.

FIGS. 8 and 9 depict various features of embodiments of the present disclosure, which embodiments are generally directed to a system that can utilize sensors or detectors to detect if a specimen/sample has been left in the sample chamber concurrently with the acquisition of an x-ray image or real-time image. The detectors may encompass laser, infrared, or weight sensors/detectors. FIGS. 8 and 9 display the basic software logic workflow of the cabinet x-ray unit that can be incorporated into computer 470. Referring first back to FIG. 1, there is shown an example of the embodiment including an electronic sample detector 30 (e.g., camera, laser, infrared or ultrasonic sensor) incorporated into a Cabinet X-Ray Unit 22. In addition to the sample detector (e.g., camera, laser detector, infrared detector, ultrasound detector) 30, a second sample detector 21 (e.g., a weight scale or pressure sensor may be used in conjunction with the sample tray 19) to sense the weight of a specimen that has been left in the chamber 28. Now referring to FIG. 8, the medical professional or other authorized operator turns on the X-ray unit 802 and the computer 470 is started, opens the door 804 places a specimen/sample 18 into the chamber 806, closes and secures the door 808, enters sample data 810 and the operator initiates scanning the specimen 812 using, for example, commands available on the computer screen. Simultaneously the computer commands the camera 30, X-ray source 14 in conjunction with the X-ray detector 20 to capture images 814, the computer stores image data from the X-ray detector 20 at 818 and display them on the monitor 824. This provides more flexibility for the operator (e.g., a clinician or other user of the system) and simplifies the procedure. Manual input for operation of the cabinet x-ray unit may also be initiated via keyboard and the resulting image from both the manual-initiated examination is displayed on the screen and configured in accordance with one example embodiment of the present disclosure. If the cabinet door is opened 825, a timer that is part of the computer 470 may not be triggered. However, there are embodiments where the opening of the cabinet door is not a factor as to whether the timer starts 826. The computer detects after "x" amount of time difference between a base image of an empty chamber at 804 versus the current state at 825 when the sample is present in the sample chamber using the electronic sample detector and/or the mass sample detector at both points in time to see if a sample has been left in the sample chamber after acquisition. In this embodiment the computer utilizes image comparison of the two images generated by the camera, but it may be a multitude of sensors for the same purpose, i.e. ultrasound, laser, infrared, camera, weight scale, pressure sensor. If after the timer starts the cabinet door opens 827, the timer may be stopped. However, there are embodiments where the opening of the cabinet door 827 is not a factor as to whether the timer stops. If the timer reaches a predetermined time (e.g., 300 seconds) and a comparison of the base image of an empty chamber at 804 versus the current state at 827 indicates that the sample has been left in the sample chamber, an error message is displayed on the computer monitor 830. If the sample has not been left in the sample chamber, no error message is displayed. Alternative embodiments may include an audio alarm separately or in combination with the error message 830.

FIG. 9 displays another embodiment of workflow of the cabinet x-ray unit to detect if a sample/specimen has been left in the sample chamber. As shown in FIG. 8, the cabinet system has power applied to it 802 and the computer 470 is started. Referring to FIG. 9, the operator opens the cabinet door 904 and inserts the specimen 18 into the cabinet. As the door is closed the software timer in computer 470 is reset to 0 at 928 and the system acquires or scan an image of the sample/specimen 912. After acquiring the x-ray image 912, the timer starts 926. If the cabinet door is not opened 927, activation of the timer 926 initiates a countdown of the pre-set time of, for example, 300 (three hundred) seconds at

929. If the door is not opened 927 within that time, the timer starts again 928 and after the pre-set time of, for example, 300 (three hundred) seconds 929 an alarm (audio or visual) and/or error message 930 is displayed on the monitor 472 and if the door is opened 927/931 within the pre-set time of, for example, the 300 (three hundred) seconds 929 then a reset 928 is performed on the timer to reinitiate the start of the timer 926/928. However, there are embodiments where after the preset time at 929 is reached, a comparison of the base image of an empty chamber versus the current state at 929 is performed to determine whether the sample has been left in the sample chamber and, if the sample has been left in the sample chamber, the error message 930 is displayed. If the sample has not been left in the sample chamber, reset 928 is performed on the timer to reinitiate the timer 928.

The above software logic is performed in the system computer 470 and takes inputs from the cabinet 400 and the keyboard 476 as well as the system door 424.

Indeed, it is appreciated that the system and its individual components can include additional features and components, though not disclosed herein as they are incorporated into an x-ray cabinet, while still preserving the principles of the present disclosure. Note also that the base computer can be one of any number devices, including a desktop or laptop computer, etc.

The present disclosure may include embodiments in other specific forms without departing from its spirit or essential characteristics. The described embodiments are to be considered in all respects only as illustrative, not restrictive. All changes that come within the meaning and range of equivalency of the claims are to be embraced within their scope.

What is claimed is:

1. A cabinet X-ray system for obtaining X-ray images of a specimen, the system comprising:
   a cabinet defining an interior chamber, the cabinet including an opening with a door to provide access to the interior chamber;
   a display;
   an audio alarm capable of generating a sound;
   a timer;
   an X-ray system including:
      an X-ray source;
      an X-ray detector;
      a specimen platform;
   at least one sample detector to determine the presence or absence of the specimen disposed on the specimen platform; and
   a controller configured to:
      receive a first set of data from the at least one sample detector before the specimen is disposed on the specimen platform;
      selectively energize the X-ray source to emit X-rays through the specimen disposed on the specimen platform to the X-ray detector;
      control the X-ray detector to collect a projection X-ray image of the specimen when the X-ray source is energized;
      selectively display the X-ray image on the display;
      start the timer after the X-ray detector has collected the projection X-ray image of the specimen;
      stop the timer after it was started if the door of the cabinet is opened after the X-ray detector has collected the projection X-ray image of the specimen;
      receive a second set of data from the at least one sample detector after the X-ray detector has collected the projection X-ray image of the specimen after the timer has elapsed a predetermined amount of time after it was started and before the timer was stopped because the door was opened after the X-ray detector has collected the projection X-ray image of the specimen;
      compare the first set of data from the at least one sample detector to the second set of data from the at least one sample detector to determine if the specimen is disposed on the specimen platform;
      generate an error code if the first set of data from the at least one sample detector and the second set of data from the at least one sample detector is different to indicate that the specimen remains disposed on the specimen platform; and
      indicate the error code using at least one of shown on the display and the audio alarm generating the sound to indicate that the specimen needs to be removed from the specimen platform.

2. The cabinet X-ray system of claim 1, wherein the at least one sample detector is a camera, a laser detector, an infrared detector, an ultrasound detector, a weight scale sensor, a strain gauge or a pressure sensor.

3. The cabinet X-ray system of claim 2, wherein the at least one sample detector is positioned in the interior chamber.

4. The cabinet X-ray system of claim 1, further comprising:
   the specimen platform having a protective cover of and in physical contact with the X-ray detector;
   a motion control mechanism configured for moving the X-ray source to or along a plurality of positions within the interior chamber relative to the specimen disposed on the specimen platform; and
   the controller further configured to:
      selectively energize the X-ray source to emit X-rays through the specimen to the X-ray detector at selected positions of the X-ray source relative to the specimen such that the isocenter of the emitted X-rays at the selected positions is located at a surface of the X-ray detector;
      control the X-ray detector to receive a collection of two-dimensional projection X-ray images of the specimen when the X-ray source is energized at the selected positions, wherein one of the two-dimensional projection X-ray images is a two-dimensional X-ray image taken at standard imaging angle of approximately 0°;
      create a tomosynthetic X-ray image reconstructed from the collection of two-dimensional projection X-ray images;
      process the collection of the two-dimensional projection X-ray images in the controller into one or more reconstructed tomosynthetic X-ray images representing a volume of the specimen and relating to one or more image planes that are selectively the same or different from that of one or more of the two-dimensional projection X-ray images;
      selectively display one or more of the two-dimensional X-ray image and the one or more reconstructed tomosynthetic X-ray images; and
      receive the second set of data from the at least one sample detector after the X-ray detector has received the collection of the two-dimensional projection X-ray images of the specimen after the timer has elapsed a predetermined amount of time after it was started and before the timer was stopped because the door was opened after the X-ray detector has received the collection of two-dimensional projection X-ray image of the specimen.

5. The cabinet X-ray system of claim 1, wherein the controller is further configured to send instructions to the at least one sample detector to transmit the first set of data from the sample detector to the controller and to transmit the second set of data from the at least one sample detector to the controller.

6. The cabinet X-ray system of claim 1, wherein the at least one sample detector is a weight scale sensor or a pressure sensor positioned proximal to or incorporated into the specimen platform.

7. A cabinet X-ray system for obtaining X-ray images, projection X-ray images and reconstructed tomosynthetic X-ray images of a specimen, the system comprising:
  a cabinet defining an interior chamber and an equipment enclosure, the cabinet including an opening with a door to provide access to the interior chamber;
  a display;
  an audio alarm capable of generating a sound;
  a timer;
  an X-ray system including:
    an X-ray source positioned in the interior chamber;
    an X-ray detector positioned in the interior chamber;
    an optical camera configured to capture an optical image of the specimen;
    a specimen platform positioned in the interior chamber and which is a protective cover of and in physical contact with the X-ray detector; and
    a motion control mechanism positioned in the interior chamber and configured for moving the X-ray source to or along a plurality of positions within the interior chamber relative to the specimen disposed on the specimen platform;
  at least one sample detector positioned in the interior chamber configured to determine the presence or absence of the specimen disposed on the specimen platform; and
  a controller positioned in the equipment enclosure and configured to:
    receive a first set of data from the at least one sample detector before the specimen is disposed on the specimen platform;
    control the optical camera to capture and collect an optical image of the specimen;
    selectively energize the X-ray source to emit X-rays through the specimen to the X-ray detector at selected positions of the X-ray source relative to the specimen such that the isocenter of the emitted X-rays at the selected positions is located at a surface of the X-ray detector;
    control the X-ray detector to receive a collection of two-dimensional projection X-ray images of the specimen when the X-ray source is energized at the selected positions, wherein one of the two-dimensional projection X-ray images is a two-dimensional X-ray image taken at standard imaging angle of approximately 0°;
    create a tomosynthetic X-ray image reconstructed from the collection of two-dimensional projection X-ray images;
    process the collection of the two-dimensional projection X-ray images in the controller into one or more reconstructed tomosynthetic X-ray images representing a volume of the specimen and relating to one or more image planes that are selectively the same or different from that of one or more of the two-dimensional projection X-ray images;
    selectively display at least one of the two-dimensional projection X-ray images, the one or more reconstructed tomosynthetic X-ray images and the optical image on the display;
    start the timer after the X-ray detector has received the collection of two-dimensional projection X-ray images of the specimen;
    stop the timer after it was started if the door of the cabinet is opened after the X-ray detector has received the collection of two-dimensional projection X-ray image of the specimen;
    receive a second set of data from the at least one sample detector after the X-ray detector has received the collection of the two-dimensional projection X-ray images of the specimen after the timer has elapsed a predetermined amount of time after it was started and not stopped because the door was not opened after the X-ray detector has received the collection of two-dimensional projection X-ray image of the specimen;
    compare the first set of data from the sample detector to the second set of data from the sample detector to determine if the specimen is disposed on the specimen platform; and
    generate an error code if the first set of data from the at least one sample detector and the second set of data from the at least one sample detector is different to indicate that the specimen remains disposed on the specimen platform; and
    indicate the error code using at least one of shown on the display and the audio alarm generating the sound to indicate that the specimen needs to be removed from the specimen platform.

8. The cabinet X-ray system of claim 7, wherein the at least one sample detector is a camera, a laser detector, an infrared detector, an ultrasound detector, a weight scale sensor, a strain gauge or a pressure sensor.

9. The cabinet X-ray system of claim 7, wherein the at least one sample detector is positioned in the interior chamber to detect the specimen on the specimen platform.

10. The cabinet X-ray system of claim 7, wherein the controller is further configured to send instructions to the at least one sample detector to transmit the first set of data from the sample detector to the controller and to transmit the second set of data from the at least one sample detector to the controller.

11. The cabinet X-ray system of claim 7, wherein the at least one sample detector is a weight scale sensor or a pressure sensor positioned proximal to or incorporated into the specimen platform.

12. A method for obtaining an X-ray image and detecting a specimen in a cabinet X-ray system, wherein the cabinet X-ray image system comprises:
  a cabinet defining an interior chamber, the cabinet including an opening with a door to provide access to the interior chamber;
  a display;
  an audio alarm capable of generating a sound;
  a timer;
  an X-ray system including:
    an X-ray source;
    an X-ray detector; and
    a specimen platform;

at least one sample detector to determine the presence or absence of the specimen disposed on the specimen platform; and a controller configured to:
- receive a first set of data from the at least one sample detector before the specimen is disposed on the specimen platform;
- selectively energize the X-ray source to emit X-rays through the specimen disposed on the specimen platform to the X-ray detector;
- control the X-ray detector to collect a projection X-ray image of the specimen when the X-ray source is energized;
- selectively display the X-ray image on the display;
- start the timer after the X-ray detector has collected the projection X-ray image of the specimen;
- stop the timer after it was started if the door of the cabinet is opened after the X-ray detector has collected the projection X-ray image of the specimen;
- receive a second set of data from the at least one sample detector after the X-ray detector has collected the projection X-ray image of the specimen after the timer has elapsed a predetermined amount of time after it was started and before the timer was stopped because the door was opened after the X-ray detector has collected the projection X-ray image of the specimen;
- compare the first set of data from the at least one sample detector to the second set of data from the at least one sample detector to determine if the specimen is disposed on the specimen platform;
- generate an error code if the first set of data from the at least one sample detector and the second set of data from the at least one sample detector is different to indicate that the specimen remains disposed on the specimen platform; and
- indicate the error code using at least one of shown on the display and the audio alarm generating a sound to indicate that the specimen needs to be removed from the specimen platform, the method comprising:
- generating a first set of data from the at least one sample detector before the specimen is disposed on the specimen platform;
- placing the specimen on the specimen platform;
- controlling the X-ray detector to collect the X-ray image of the specimen when the X-ray source is energized;
- starting the timer after the X-ray detector has collected the projection X-ray image of the specimen;
- stopping the timer after it was started if the door of the cabinet is opened after the X-ray detector has collected the projection X-ray image of the specimen;
- generating a second set of data from the at least one sample detector after the X-ray detector has collected the X-ray image of the specimen after the timer has elapsed a predetermined amount of time after it was started and before the timer was stopped because the door was opened after the X-ray detector has collected the projection X-ray image of the specimen;
- comparing the first set of data from the at least one sample detector to the second set of data from the at least one sample detector to determine if the specimen is disposed on the specimen platform;
- generating an error code if the first set of data from the at least one sample detector and the second set of data from the at least one sample detector is different to indicate that the specimen remains disposed on the specimen platform;
- indicating the error code using at least one of shown on the display and the audio alarm generating a sound to indicate that the specimen needs to be removed from the specimen platform; and
- removing the specimen from the specimen platform after the error code is indicated using at least one of shown on the display and the audio alarm generating a sound.

13. The method of claim 12, wherein the at least one sample detector is a camera, a laser detector, an infrared detector, an ultrasound detector, a weight scale sensor, a strain gauge or a pressure sensor.

14. The method of claim 13, wherein the at least one sample detector is positioned in the interior chamber.

15. The method of claim 12, wherein the controller is further configured to send instructions to the at least one sample detector to transmit the first set of data from the sample detector to the controller and the second set of data from the at least one sample detector to the controller and the method further includes sending instructions from the controller to the at least one sample detector to generate and transmit the first set of data from the at least one sample detector to the controller and sending instructions from the controller to the at least one sample detector to generate and transmit the second set of data from the at least one sample detector to the controller.

* * * * *